(12) United States Patent
Sauer et al.

(10) Patent No.: US 8,202,427 B2
(45) Date of Patent: Jun. 19, 2012

(54) POROUS FERRO-OR FERRIMAGNETIC GLASS PARTICLES FOR ISOLATING MOLECULES

(75) Inventors: Philippe Sauer, Sulzbach (DE); Bernd Springer, Wülfrath (DE); Thomas Manz, Düsseldorf (DE); Christoph Ritt, Langenfeld (DE); Roland Fabis, Leverkusen (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 13/034,217

(22) Filed: Feb. 24, 2011

(65) Prior Publication Data

US 2011/0186524 A1 Aug. 4, 2011

Related U.S. Application Data

(62) Division of application No. 11/635,304, filed on Dec. 7, 2006, now Pat. No. 7,922,917, which is a division of application No. 10/239,112, filed as application No. PCT/EP01/03294 on Mar. 22, 2001, now Pat. No. 7,183,002.

(60) Provisional application No. 60/192,093, filed on Mar. 24, 2000.

(51) Int. Cl.
*B01D 11/00* (2006.01)

(52) U.S. Cl. ........ 210/638; 210/639; 210/690; 210/695; 435/4; 435/6.1

(58) Field of Classification Search ........... 210/634, 210/635, 638, 639, 656, 695, 670, 691, 692, 210/690; 435/6, 6.1, 4; 436/178; 65/21.1, 65/21.4, 142; 428/402–404, 406; 502/407
See application file for complete search history.

(56) References Cited

U.S. PATENT DOCUMENTS

| | | |
|---|---|---|
| 3,549,524 A | 12/1970 | Haller |
| 3,758,284 A | 9/1973 | Haller |
| 4,126,437 A | 11/1978 | O'Horo |
| 4,169,804 A | 10/1979 | Yapel, Jr. |
| 4,233,169 A | 11/1980 | Beall et al. |
| 4,297,337 A | 10/1981 | Mansfield et al. |
| 4,309,459 A | 1/1982 | Tokuoka |
| 4,310,253 A | 1/1982 | Sada et al. |
| 4,329,241 A | 5/1982 | Massart |
| 4,335,094 A | 6/1982 | Mosbach |
| 4,395,271 A | 7/1983 | Beall et al. |
| 4,438,068 A | 3/1984 | Forrest |
| 4,554,088 A | 11/1985 | Whitehead et al. |
| 4,628,037 A | 12/1986 | Chagnon et al. |
| 4,895,650 A | 1/1990 | Wang |
| 4,988,618 A | 1/1991 | Li et al. |
| 5,512,332 A | 4/1996 | Liberti et al. |
| 5,523,231 A | 6/1996 | Reeve |
| 5,601,979 A | 2/1997 | Wong |
| 5,610,274 A | 3/1997 | Wong |
| 5,665,554 A | 9/1997 | Reeve et al. |
| 5,681,946 A | 10/1997 | Reeve |
| 5,734,020 A | 3/1998 | Wong |
| 5,904,848 A | 5/1999 | Wong et al. |
| 5,945,525 A | 8/1999 | Uematsu et al. |
| 6,027,945 A | 2/2000 | Smith et al. |
| 6,255,477 B1 | 7/2001 | Kleiber et al. |
| 6,296,937 B2 | 10/2001 | Pryor et al. |
| 6,447,911 B1 | 9/2002 | Pryor et al. |
| 6,607,677 B1 | 8/2003 | Buchecker et al. |
| 7,183,002 B2 | 2/2007 | Sauer et al. |
| 7,922,917 B2 * | 4/2011 | Sauer et al. ........... 210/770 |

FOREIGN PATENT DOCUMENTS

| | | |
|---|---|---|
| DE | 43 07 262 | 9/1994 |
| EP | 0 389 063 | 9/1990 |
| EP | 0757106 | 2/1997 |
| JP | 61039509 | 2/1986 |
| WO | WO 91/12079 | 8/1991 |
| WO | WO 93/10162 | 5/1993 |
| WO | WO 94/11103 | 5/1994 |
| WO | WO 95/01359 | 1/1995 |
| WO | WO 96/41811 | 12/1996 |
| WO | WO 98/12717 | 3/1998 |
| WO | WO 98/31461 | 7/1998 |
| WO | WO 98/31840 | 7/1998 |
| WO | WO 98/51435 | 11/1998 |

OTHER PUBLICATIONS

White, et al., "Magnesil Paramagnetic Particles: Novel Magnetics for DNA Purification," Promega Notes No. 69 (1998), pp. 12-15.
Notice of Opposition, submitted in EP 1 266 385/01 938 032.8 (Sep. 30, 2009), 30 pages, no author.
Reply to Notice of Opposition, submitted in EP 1 266 385/01 938 032.8 (May 14, 2010) 41 pages, no author.
Electron Microscopy Images of the "Boehringer Particle" submitted in Reply to Notice of Opposition, submitted in EP 1 266 385/01 938 032.8 (May 14, 2010), 2 pages, no author.
Electron Microscopy Images of Particles Manufactured According to the Opposed Patent submitted Reply to Notice of Opposition, submitted in EP 1 266 385/01 938 032.8 (May 14, 2010), 2 pages, no author.
Alderton, et al., Analytical Biochemistry, 201:166-169 (1992).

(Continued)

*Primary Examiner* — Joseph Drodge
(74) *Attorney, Agent, or Firm* — Fanelli Haag & Kilger PLLC

(57) ABSTRACT

Porous, ferro- or ferrimagnetic, glass particles are described that selectively bind molecules of interest, especially nucleic acid molecules; under appropriate conditions. Methods of preparing the porous, ferro- or ferrimagnetic, glass particles and their use for identifying or separating molecules of interest are also described. Kits comprising the porous, ferro- or ferrimagnetic, glass particles are also provided.

22 Claims, No Drawings

OTHER PUBLICATIONS

Bean, et al., Journal of Applied Physics, 30(4): 120S-129S (1959).
Homola, et al., IEEE Transactions on Magnetics, MAG- 22(5): 716-719 (1986).
Sugimoto, et al., Journal of Colloid and Interface Science, 74(1): 227-243 (1980).
Unger K., Journal of Chromatography Library, 16:1-83 (1988).

* cited by examiner

POROUS FERRO-OR FERRIMAGNETIC GLASS PARTICLES FOR ISOLATING MOLECULES

CROSS-REFERENCE TO RELATED APPLICATIONS

This application is a divisional application of U.S. Ser. No. 11/635,304, filed Dec. 7, 2006, now U.S. Pat. No. 7,922,917, which is a divisional application of U.S. Ser. No. 10/239,112, filed Jan. 16, 2003, now U.S. Pat. No. 7,183,002, which is a United States national stage filing under 35 U.S.C. §371 of international application No. PCT/EP01/03294, filed Mar. 22, 2001, which claims priority to U.S. Provisional Application No. 60/192,093, filed Mar. 24, 2000. The disclosure of each of which is incorporated by reference herein in its entirety.

In recent years, magnetic particles of various compositions and properties have become available to facilitate purification, separation, and assay of various molecules. Magnetic particles or beads that bind a molecule of interest can be collected or retrieved by applying an external magnetic field to a vessel containing the particles. Unbound molecules and supernatant liquid can be separated from the particles or discarded, and the molecules bound to the particles may be eluted in an enriched state. Thus, magnetic particles offer the potential for a relatively rapid, easy, and simple means to purify or separate molecules of interest from a liquid phase or a mixture of other molecules. Furthermore, magnetic particles that bind specific molecules may be integrated into robotic, multi-well, or multiplex sample assays or screening systems to rapidly and automatically assay or identify molecules of interest out of hundreds or even thousands of samples. Such systems are finding increasingly more applications in the purification or isolation of biomolecules, such as nucleic acids and protein. Accordingly, a magnetic particle with an increased capacity to bind and isolate molecules, especially biomolecules, of interest would serve as a valuable tool in a variety of separation or isolation applications, including analytical and preparative procedures, as well as in mechanized systems designed to automatically screen arrays of hundreds or even thousands of samples for a particular molecule or class of molecules of interest.

The invention provides highly porous, ferromagnetic or ferrimagnetic, glass (silica) particles that exhibit high binding capacities for molecules of interest, especially biomolecules, and, most preferably, nucleic acid molecules. The porous, ferro- or ferrimagnetic, glass particles of the invention can bind molecules, especially nucleic acid molecules, in a mixture, and then be collected or retrieved while still retaining the bound molecules by applying an external magnetic field to a side of a vessel containing the mixture and the magnetic particles or by inserting a magnetic probe into the vessel. The bound molecules may then be eluted from the magnetic particles in a purer state and in useful amounts owing to the high binding capacity of the magnetic particles of the invention for the molecules of interest.

The porous, ferro- or ferrimagnetic, glass particles of the invention comprise silicon dioxide ($SiO_2$) and iron oxide particles or pigments. The iron oxide particles or pigments may be, e.g., $Fe_2O_3$ (hematite), $Fe_3O_4$ (magnetite), or a combination thereof. Preferably, the iron oxide is ferrimagnetic magnetite.

In another embodiment of the invention, the porous, ferro- or ferrimagnetic, glass particles of the invention have a composition that is about 30-50% (by weight) $Fe_3O_4$ and about 50-70% (by weight) $SiO_2$. More preferably, the composition of the porous, magnetic, glass particles described herein is about 35-45% (by weight) $Fe_3O_4$ and about 55-65% (by weight) $SiO_2$.

In yet another embodiment, one or more oxides of other metals or transition metals may also be present in the porous, magnetic, glass particles of the invention. Such additional metal oxides may provide additional desirable properties to the porous, magnetic, glass particles. Preferably, an additional metal oxide is selected from the group consisting of oxides of titanium, boron, sodium, potassium, magnesium, calcium, zinc, lead, and combinations thereof.

The porous, magnetic, glass particles of this invention show ferro- or ferrimagnetic behavior due to the presence of iron oxides or iron bearing pigments. If an external magnetic field is applied, they are magnetized and remain magnetized (remanence) even when the external magnetic field is removed, but this remaining magnetism is too weak to agglomerate or aggregate the particles.

In another aspect of the invention, the porous, magnetic, glass particles described herein have an average size range of about 5-25 µm, preferably about 6-15 µm, and, most preferably, about 7-10 µm in diameter. Preferably, the total surface area of the porous, magnetic, glass particles of the invention, as measured by the nitrogen Brunaur Emmet Teller (BET) method, is 190 $m^2/g$ or greater and, more preferably, in the range of about 190-270 $m^2/g$. Preferably, the porous, magnetic, glass particles of the invention have a cumulative pore area for pores greater than 10 nm in diameter, as measured by the mercury (Hg)-porosimetry method, that is in the range of about 4-8 $m^2/g$.

In another aspect of the invention, methods for manufacturing porous, magnetic, glass particles with high binding capacities for nucleic acids, or other biomolecules, are provided. A preferred manufacturing process of the invention comprises providing a suspension of magnetic iron oxide particles or pigments having an average size of 75-300 nm in diameter. More preferably, 80% or more, and even more preferably, 90% or more, of the iron oxide particles are 75-300 nm in diameter. Preferably, the iron oxide particles are suspended in glycerol or glycol, and combined with a source of silica (glass), and preferably at a pH in the range of 6 to 8, and more preferably pH 7. Silica is then synthesized in the presence of the iron oxide particles by hydrolyzing the source of silica with acidic or alkaline buffer so that the silica precipitates or adsorbs on the surface of the iron oxide particles. The silica-coated iron oxide particles are allowed to aggregate to form larger, porous, magnetic, glass particles. The nascent porous, magnetic, glass particles are then dried using an oven at a temperature below the Curie temperature. More preferably, the drying temperature is between about 100° C. and about 500° C., such as 200° C. or 300° C. Even more preferably, the drying temperature is between about 300° C. and about 500° C.

In another embodiment of the manufacturing methods of the invention, the source of silica is a tetraalkoxysilane, a silyl ester of a multifunctional alcohol, a silicate, such as sodium silicate, silica nanoparticles, or combinations thereof. More preferably, the source of silica is a tetraalkoxysilane, and most preferably, the tetraalkoxysilane is tetraethoxysilane.

In yet another embodiment of the manufacturing process of the invention, the source of silica is hydrolyzed in the manufacturing process using a buffer that has an acidic pH of 5 or lower or a buffer that has an alkaline pH of 9 or higher. Preferably, the hydrolyzing buffer is an ammonia/ammonium salt buffer having a pH of between 9 and 11.

In a preferred embodiment, porous, ferro- or ferrimagnetic, glass particles of the invention bind greater than 1 µg of nucleic acid molecules per mg of particle, even more preferably about 1.3 μg of nucleic acid molecules per mg of particle, and most preferably greater than 1.3 μg of nucleic acid molecules per mg of particle.

In another embodiment, the yields of nucleic acid molecules isolated using the porous, ferro- or ferrimagnetic, glass particles of the invention are 80% or greater.

Another aspect of the invention is a method for isolating a molecule of interest from a mixture, comprising:

providing a mixture containing the molecule of interest;

contacting the mixture with porous, ferro- or ferrimagnetic, glass particles of the invention;

allowing the molecule of interest in the mixture to bind or adhere to the porous, ferro- or ferrimagnetic, glass particles;

collecting the porous, ferro- or ferrimagnetic, glass particles containing the adherent molecule of interest by applying an external magnetic field; and separating the porous, ferro- or ferrimagnetic, glass particles with the adherent molecule of interest from the unbound components of the mixture.

Optionally, the bound molecule of interest may be eluted from the particles of the invention by using an appropriate elution buffer.

In a preferred embodiment of the methods of isolating or separating a molecule of interest from a mixture using the porous, ferro- or ferrimagnetic, glass particles of the invention, the molecule of interest is selected from the group consisting of nucleic acids, proteins, polypeptides, peptides, carbohydrates, lipids, and combinations thereof. More preferably, the molecule of interest is a nucleic acid molecule, which may be any nucleic acid molecule, including plasmid DNA, genomic DNA, cDNA, polymerase chain reaction-generated DNA (PCR DNA), linear DNA, RNA, ribozymes, aptamers, and chemically synthesized nucleic acid molecules.

In another embodiment, the invention provides kits for isolating or separating molecules of interest, preferably nucleic acid molecules of interest, comprising porous, ferro- or ferrimagnetic, glass particles of the invention. A kit of the invention may further comprise one or more buffers or concentrated stock solutions for suspending and using the porous, magnetic, glass particles of the invention. A buffer in a kit of the invention may also contain one or more chaotropic agents, such as guanidinium isothiocyanate.

The porous, ferro- or ferrimagnetic, glass (silica) particles described herein have a relatively high binding capacity for various molecules, and especially nucleic acids, such that the particles are useful in isolating or separating molecules from a mixture in useful yields. The particles may be used in both analytical as well as preparative scale procedures. Particles having a particular porosity, binding capacity, and binding specificity are obtained by selectively changing various synthetic reaction parameters according to the invention.

In order that the invention may be more fully understood, the following terms are defined.

"Pore", as understood and used herein, refers to any inlet, depression, or recess in the outer surface of a particle in which the depth of the depression or recess extends beyond the length of the radius of the inlet, depression, or recess measured at the surface of the particle. Inlets, depressions, or recesses that do not extend deeper than the radius at the outer surface of the particle are not pores.

"Micropore", as understood and used herein, refers to any pore that has an average diameter of less than 2 nm.

"Mesopore", as understood and used herein, refers to any pore that has an average diameter in the range of 2 nm-200 nm.

"Macropore", as understood and used herein, refers to any port that has an average diameter of greater than 200 nm.

"Diameter of a pore", as understood and used herein, refers to the diameter of the pore at the narrowest point of the respective pore.

"Size of a particle", as understood and used herein, refers to the diameter of a particle. For a spherical particle, the size corresponds to its diameter. More generally, the size of regularly or irregularly shaped particles refers to the projected area of the diameter of the particle, expressed by the diameter of a circle with the same area as that of the particle resting in a stable position.

"Cumulative pore area", as understood and used herein, refers to the calculated total pore area of pore walls, for pores having a certain diameter (size).

"Surface area", as understood and used herein, refers to the surface area of a porous particle, which is equal to the sum of its inner and outer surface areas.

"Outer surface" of a particle, as understood and used herein, refers to each and every point of a particle from which a line that is perpendicular to that point is able to extend outward without intersecting another portion of the particle.

"Inner surface", of a porous particle, as understood and used herein, refers to the surface that originates from the pore walls.

"Paramagnetic" substances, as understood and used herein, exhibit a weak magnetic property only in the presence of an applied magnetic field. In the absence of an applied magnetic field, the spin and orbital moments are unaligned; pointing randomly to cancel each other out. However, in the presence of an externally applied magnetic field, spin and orbital moments tend to turn toward the direction of the field. However, thermal agitation of atoms of paramagnetic substances opposes the tendency for all the magnetic moments to align. The result is only partial alignment of the moments in the direction of the applied magnetic field. As long as the magnetic field is applied, the substance will exhibit a net, but relatively weak, magnetic field. When the external magnetic field is removed, the partial alignment deteriorates, and no magnetic field survives in the substance.

Like paramagnetic substances, "superparamagnetic" substances, as understood and used herein, also exhibit an induced and temporary magnetic field in the presence of an externally applied magnetic field. In truly superparamagnetic substances, the magnetic moments of individual atoms of the substance are able to align and add up to form a much stronger induced magnetism than is possible in a paramagnetic substance (see, for example, Bean and Livingstone, *J. Appl. Physics*, 30: 120S-129S (1959)). Thus, the induced magnetic field of superparamagnetic substances is significantly stronger (by several orders of magnitude) than the fields generated in substances classically defined as "paramagnetic". Iron oxide crystals of less than about 300 angstroms (30 nm) in diameter are capable of exhibiting such superparamagnetic behavior.

"Ferromagnetic" substances, e.g., hematite ($Fe_2O_3$), $Fe_{Metal}$, Ni, Co, as understood and used herein, are substances that are capable of exhibiting a magnetic field even in the absence of an applied magnetic field. In ferromagnetic substances, regions or domains of the substance are capable of aligning magnetic moments in the same direction resulting in a magnetic field. If an external magnetic field is applied to a ferromagnetic substance, the various domains of the substance can become aligned in the same direction to yield a very strong magnetic field in the ferromagnetic substance. Even if the external magnetic field is removed, the domains of the ferromagnetic substance tend to remain aligned in the same direction and so the substance as a whole retains a strong magnetic field, essentially unperturbed by any innate thermal agitation. However, by heating a ferromagnetic substance to a sufficiently high temperature, thermal energy can exceed the magnetization energy so that the alignment of magnetic moments deteriorates and becomes random. At such temperatures, the substance is capable of exhibiting a paramagnetic behavior in the presence of an exogenously applied magnetic field. The temperature at which a ferromagnetic substance becomes paramagnetic is known as the "Curie temperature" or "Curie point".

"Ferrimagnetic" substances, as understood and used herein, exhibit a magnetic field that is retained (remanence) after being exposed to an externally applied magnetic field, similar to ferromagnetic substances. Ferrimagnetism is the magnetic property that is only found in ferrites, which are mixed oxides $(M^{2+}O)(Fe_2O_3)$, where one cation is a divalent ion ($M^{2+}$) from the group of transition metals, e.g., $Fe^{2+}$, $Mn^{2+}$, $Zn^{2+}$, $Co^{2+}$, etc., and the trivalent cation is $Fe^{3+}$, e.g., magnetite ($Fe_3O_4$). The crystal structure of ferrites consists of two interlocking crystals. When the spins of the atoms of one lattice position are aligned in a particular orientation and the spins of atoms in another position are aligned in an opposite orientation, a magnetic field will be retained (remanence). Thus, ferrimagnetic substances are crystalline ferric oxide compounds, which resemble ferromagnetic substances in their ability to retain a magnetic field in the absence of an externally applied magnetic field.

The porous, magnetic, silica particles of this invention show ferro- or ferrimagnetic behavior and remain magnetized even in the absence of an external magnetic field, but this remaining magnetism is too weak to agglomerate or aggregate the particles.

Unless noted otherwise, the terms "silica", "silica glass", and "glass", as understood and used herein, refer to an amorphous, crystalline form of $SiO_2$ that covers all or a portion of the iron oxide particles or pigments that are used to make the porous, ferro- or ferrimagnetic, glass particles of this invention.

The porous, ferro- or ferrimagnetic, glass particles of the invention are useful for isolating or separating nucleic acid molecules from any mixture or sample. A "mixture" or "sample", as understood and used herein, includes any mixture or preparation that contains a molecule of interest, whether the mixture is man-made or derived from a natural or biological source, such as cells, tissues, or viruses. A mixture or sample may be complex, e.g., containing many components in addition to a molecule of interest, or relatively simple, such as an aqueous solution of a molecule of interest. A mixture includes, but is not limited to, any of the various in vitro reaction mixtures used to manipulate or synthesize nucleic acids or that contain nucleic acids, such as polymerase chain reaction (PCR), nucleic acid sequencing reactions, restriction endonuclease or other nuclease digestion reactions, nucleic acid hybridization assay mixtures, protein-nucleic acid binding assay mixtures, antibody-nucleic acid assay mixtures, and in vitro transcription and/or translation assay mixtures. A biological material that may be in a mixture or sample includes, but is not limited to, blood, plasma, lymph, milk, urine, semen, or other biological fluids, whole cells, extracts of cells, viral particles, hair, and tissue homogenates.

Compositions and Methods of Manufacturing Porous, Magnetic, Glass Particles

The porous, ferro- or ferrimagnetic, glass particles of this invention contain iron oxide and silica glass. Preferably, the particles have a relatively simple composition that is 30-50% (by weight) $Fe_3O_4$ and 50-70% (by weight) $SiO_2$. More preferably, the particles of this invention are 35-45% (by weight) $Fe_3O_4$ and 55-65% (by weight) $SiO_2$. However, other compounds may be incorporated into the reaction mixtures to obtain particles having properties that are better suited for a particular protocol. Accordingly, in addition to iron oxide, The particles of this invention may also contain oxides of other metals, especially transition metals, and include, without limitation, oxides of titanium, boron, sodium, potassium, magnesium, calcium, zinc, and lead. Preferably, iron oxide is the most prevalent metal oxide by weight in the particles of this invention.

The size of the iron oxide particles or pigments used in the manufacturing process affects the size and characteristics of the final particle product. For this reason, the component iron oxide particles or pigments preferably have an average size in the range of about 75 to 300 nm in diameter. More preferably, at least 80% of the iron oxide particles have an average size in the range of about 75 to 300 nm in diameter. Even more preferably, at least 90% of the iron oxide particles have an average size in the range of about 75 nm to 300 nm in diameter, and, most preferably, at least 95% of the iron oxide particles used to make the porous, magnetic glass particles of this invention are in this size range.

The pores of the porous, magnetic, glass particles described herein are present in a wide range of sizes as determined by the diameter of the pores at the outer surface of the particles. The high pore content of the particles of the invention, is also appreciated by the fact that particles of the invention, which are preferably in the range of about 5 to 25 μm in diameter, more preferably about 6 to 15 μm in diameter, and most preferably, about 7 to 10 μm in diameter, also have relatively high values for the BET specific surface area of 190 $m^2/g$ or greater and, preferably, in a range of 190-270 $m^2/g$; indicative of a high pore surface area for particles of this size. Thus, pores classified as micropores, mesopores, and macropores may be all represented on each particle prepared according to the invention. Notably, the pores present in the particles described herein include pores with diameters greater than and less than 10 nm in diameter. The high porosity of the porous, magnetic, glass particles of the invention is also appreciated by the fact that the cumulative pore area of the particles as determined by standard mercury porosimetry for pores greater than 10 nm in diameter is typically greater than 4 $m^2/g$ and, preferably, in the range of about 4 to 8 $m^2/g$.

The iron oxide particles or pigments constitute the basic magnetic nuclei of the porous, magnetic, glass particles of the invention. As silica is deposited or precipitated on to the iron oxide particles during the manufacturing process, the iron oxide particles begin to aggregate to form the larger, porous, magnetic, glass particles of the invention which, as noted above, have large surface areas. Unless already available in the preferred average size range of about 75 to 300 nm in diameter, the iron oxide particles or pigments may have to be reduced to the preferred size prior to carrying out the manufacturing process. The iron oxide particles or pigments may be processed to the preferred average range of sizes of about 75 nm to about 300 nm in diameter using any of a variety of methods known in the art. For example, the iron oxide particles or pigments may be ground down to an appropriate size using a ball mill, such as a PM 400 planetary ball mill (Retsch, Haan, Germany). More preferably, the iron oxide particles are ground by rapid stirring, for example, by using a commercially available stirrer for laboratory use. The iron oxide particles or pigments should be suspended in an aliphatic $C_1$-$C_6$-alcohol, more preferably, an aliphatic $C_1$-$C_4$-alcohol, such as isopropanol, ethanol, glycol, or glycerol. Preferably, glycerol is used because its higher viscosity allows preparation of smaller iron oxide particles. Most preferably, the iron oxide particles are ground to the average size range of about 75 nm to about 300 nm by rapid stirring in a solution of glycerol (e.g., 43% glycerol).

The silica component of the porous, magnetic, glass particles described herein is generated during the manufacturing procedure from a tetraalkoxysilane, preferably having the formula $Si(OC_nH_{2n+1})_4$, where n is an integer of 1-5. This silica synthesis step may also use silyl esters of multifunctional alcohols, such as glycerol and glycol. In another embodiment of the invention, the silica source may be a silicate, more preferably, a sodium silicate or silica nanoparticles. Alternatively, the source of silica may be a combination of at least one tetraalkoxysilane and at least one silyl ester of a multifunctional alcohol. Most preferably, the source of silica for the porous, magnetic, glass particles of this invention is tetraethoxysilane.

In a preferred embodiment of the manufacturing procedure, tetraalkoxysilane is added to a suspension of ferro- or ferrimagnetic iron oxide particles, as a solution of tetraethoxysilane (30%) in an aliphatic $C_1$-$C_6$ alcohol, more preferably an aliphatic $C_1$-$C_5$ alcohol, (70%) at a pH between 6 and 8, more preferably pH 7.

During the process of manufacturing the porous, magnetic, glass particles of the invention, tetraalkoxysilane, silyl ester of a multifunctional alcohol, or a combination thereof, is hydrolyzed to release silica by changing the pH of the reaction mixture to an acidic pH, e.g., pH 6 and lower, or to an alkaline pH, e.g., pH 9 and higher. Acidic buffers that may be used to hydrolyze a tetraalkoxysilane include, but are not limited to, acetate buffers that have a pH of 5. Alkaline buffers that may be used to hydrolyze the tetraalkoxysilane in the methods of the invention, include but are not limited to ammonia/ammonium salt buffers (for example, ammonia/ammonium chloride buffer) that have a pH in the range of 9 to 11. Preferably, silica is synthesized using an alkaline buffer to hydrolyze the tetraalkoxysilane to release silica. More preferably, the silica is synthesized using an ammonia/ammonium salt buffer at a pH of between 9-11.

In another embodiment of the process of manufacturing the porous, magnetic, glass particles of the invention, a silicate or silica nanoparticles are hydrolyzed to release silica by changing the pH of the reaction mixture to an acidic pH, e.g., pH 6 and lower. More preferably, the silica is synthesized using acetic acid.

The silica released upon hydrolysis of the tetraalkoxysilane or other source of silica precipitates, deposits, or adsorbs on the surface of the iron oxide particles or pigments, which then aggregate to form the larger, porous, magnetic, glass particles of the invention.

To carry out the silica synthesis step, the iron oxide particles or pigments may be mixed first with the source of silica and then the hydrolysis buffer of acidic or alkaline pH added, or the iron oxide particles may be mixed first with the hydrolysis buffer and the silica source added thereafter. However, the preferred procedure is to first mix the iron oxide particles with the silica source, and, thereafter, add the hydrolyzing buffer. In addition, the silica synthesis step is preferably carried out in a final reaction solution that is viscous enough to promote the production of small silica particles, which are able to more efficiently deposit or precipitate over the surface of the iron oxide particles. In a preferred embodiment, ammonia/ammonium chloride buffer (5 M, pH 10.5) is added dropwise to iron oxide particles, which are dispersed in a solution of glycerol (43%), ethanol (43%), and tetraethoxysilane, over a time period of ten (10) minutes while stirring the mixture at 2000 rpm. Adding the buffer over a period of time shorter than 10 minutes tends to produce unmagnetic particles, whereas adding the buffer over a longer time period tends to produce particles with a reduced porosity that are too compact and less than optimal for isolating or separating nucleic acid molecules from a sample. Stirring at lower speeds, such as 500 rpm, during silica synthesis results in porous, magnetic, glass particles that have lower binding capacities for nucleic acids.

As silica is synthesized by hydrolysis of tetraalkoxysilane or other silyl ester compound, it precipitates or adsorbs on the surface of the iron oxide particles. The silica containing iron oxide particles will then aggregate to form larger, porous, magnetic, glass (silica) particles. It is recommended that the newly formed particles be allowed to further incubate ("age") so that they may solidify or stabilize. An effective aging step may involve simply allowing the newly formed particles to continue to incubate in the silica synthesis mixture with stirring for an additional 8 to 24 hours.

The stabilized, newly formed particles are separated from the reaction mixture by filtration and then washed with a solvent solution, usually an alcohol solution. The wash solution may contain other solvents and agents in addition to or in place of alcohol, including acetone and/or a chaotropic agent (s). In general, however, an anhydrous alcohol, especially absolute ethanol, alone is preferred for washing the newly formed particles. An anhydrous alcohol, such as absolute ethanol, is highly effective at preventing agglomeration of newly formed particles and in producing particles that have or retain a high binding capacity for nucleic acid molecules.

After filtration and washing, the newly formed porous, magnetic, glass particles can be dried. Optimal drying temperatures are always below the Curie temperature and may be as low as about 100° C. or as high as about 500° C. Preferably, the temperature is in the range of about 300° C. to 500° C., such as 200° C. More preferably, optimal results are obtained by drying the newly formed particles at about 300° C. in a circulating air, drying oven. The preferred average size of the final porous, magnetic, glass particles is about 5 to 25 μm, more preferably about 6 to 15 μm, and most preferably, about 7 to 10 μm in diameter. The dried particles may be stored in an enclosed vessel at room temperature for months without showing signs of aging, i.e., deterioration of any properties of the particles.

Another method of making the ferro- or ferrimagnetic particles according to the invention comprises the steps of providing a suspension of ferro- or ferrimagnetic iron oxide particles in alcohol, preferably ethanol, adding silica nanoparticles to the suspension of the ferro- or ferrimagnetic iron oxide particles at a pH lower than 6, aging the mixture by continuous stirring, separating, e.g., magnetically; the resulting porous, ferro- or ferrimagnetic, glass particles from the liquid, washing the separated porous, ferro- or ferrimagnetic, glass particles, and drying the porous, ferro- or ferrimagnetic, glass particles at a temperature at about 200° C.

The following guidelines are recommended to produce highly porous, magnetic, glass particles that exhibit high binding capacities for nucleic acid molecules. Preferably, the iron oxide particles or pigments used in the synthesis of the porous, magnetic, glass particles of the invention are ferrimagnetic magnetite ($Fe_3O_4$) particles. The iron oxide particles or pigments should have an average size in the range of 75 nm to 300 nm in diameter. It may be necessary to reduce the size of the iron oxide particles or pigments to this recommended size range by grinding. Although ball milling may be used to grind the iron oxide particles or pigments down to the recommended size range, the grinding step preferably is carried out by rapid stirring, such as at 2000 rpm, and in a viscous solution, such as a glycerol solution. Silica is synthesized by hydrolysis of a tetraalkoxysilane, silyl ester, or silicate, or by precipitation of silica nanoparticles using an acidic or alkaline buffer. Tetraethoxysilane is the preferred source of silica for synthesizing the particles of the invention. The silica synthesis should be carried out in a viscous solution, for example, a solution containing glycerol, to promote synthesis of small silica particles, which are able to more efficiently cover or precipitate on the surface of the iron oxide particles or pigments. Preferably, the hydrolysis buffer is added to the iron oxide particles suspended in a viscous tetraalkoxysilane or silyl ester compound mixture. Furthermore, the source of silica, especially if the source is tetraethoxysilane, should be added over a period of ten (10) minutes. Anhydrous alcohol, especially absolute ethanol, is the preferred solvent for washing the newly formed porous, magnetic, glass particles. The newly formed, porous, magnetic, glass particles should be aged to allow them to stabilize. Finally, the newly formed particles should be dried at relatively high temperatures, but below the Curie temperature, in an oven between 100° C. and 500° C., preferably between 300° C. and 500° C., and even more preferably at 300° C.

Porous, ferro- or ferrimagnetic, glass particles of the invention may also be provided in a kit for separating, detecting, or isolating any of variety of molecules of interest in a mixture including, but not limited to, nucleic acids, proteins, polypeptides, peptides, carbohydrates, lipids, and combinations thereof. Preferably, the kits of the invention comprise porous, ferro- or ferrimagnetic, glass particles described herein for separating, detecting, or isolating nucleic acid molecules of interest or molecules containing nucleotides in a mixture. The kits of the invention may also include one or more buffers that are useful for suspending the porous, magnetic, glass particles and/or for later steps in the isolation or purification procedure for the nucleic acid or other molecule of interest. One or more buffers that may be included in the kits of the invention may contain one or more chaotropic agents or substances. According to this invention, preferred chaotropic agents include, without limitation, salts from the group of trichloroacetates, thiocyanates (including guanidinium (or "guanidine") isothiocyanate), perchlorates (such as sodium perchlorate), iodides (such as sodium iodide, potassium iodide), guanidinium hydrochloride, and urea. The chaotropic agents are preferably used in a range of 1 to 8 M aqueous solution, more preferably in a range of 2 to 5 M aqueous solution, and most preferably in a range of 2 to 4 M aqueous solution. Most preferably, the chaotropic agent in a buffer of a kit of the invention is guanidinium isothiocyanate.

Use in Isolating Nucleic Acids and Other Biomolecules

The porous, magnetic, glass particles described herein have a high capacity to bind nucleic acids, thereby making the particles of this invention especially useful for isolating or separating nucleic acid molecules from various samples and mixtures. The particles may also be used to isolate or separate other molecules including, but not limited to, carbohydrates, polypeptides, peptides, lipids, and even combinations of such molecules, such as glycoproteins and nucleic acid/protein combinations or assemblies. The selective isolation or separation of one molecule over another may be achieved by adjusting the buffer conditions at which a molecule of interest binds or elutes from the porous, magnetic, glass particles described herein. The magnetic property of the porous, magnetic, glass particles of the invention permits the particles to be easily and rapidly collected from a sample or mixture by applying an external magnetic field using any of a variety of magnetic collection systems available in the art.

For example, the porous, magnetic, glass particles of the invention may be used to isolate or separate any of a variety of nucleic acid molecules including, but not limited to, cDNA, PCR reaction products, plasmids, genomic nucleic acids, nucleic acid primers, various species of RNA, ribozymes, aptamers, nucleic acid molecules containing synthetically produced nucleotides, chemically synthesized nucleic acids, nucleic acid-protein complexes, hybridized nucleic acid molecules, nucleic acid molecules in in vitro transcription and/or translation assays, and immunoassays, such as ELISA or radioimmune assays, where such procedures contain a nucleic acid component. Synthetically produced nucleotides include nucleotides that have constituent moieties, i.e., sugar, nitrogenous heterocyclic base (purine or pyrimidine), and phosphate backbone, that are found in nature as well as nucleotide compounds that have a constituent moiety that has been modified or substituted with a group not found in nature. For example, the particles of the invention may be used to isolate a nucleic acid molecule that contains a synthetic nucleotide in which a thiol group replaces one or more phosphate groups, a modified purine or pyrimidine replaces a naturally occurring purine or pyrimidine, or a different molecule replaces the ribose or 2-deoxyribose sugar moiety. The particles described herein also may be used to effectively stop a reaction that depends on the presence of a nucleic acid molecule by binding and separating the nucleic acid from the reaction. In addition, the particles described herein may be used to collect or scavenge valuable or hazardous nucleic acid molecules, for example, as may be the case in forensic samples, archeological samples, accidental spills, and breaches in containment vessels.

The porous, magnetic, glass particles of the invention may be used to preferentially separate a particular class or size of nucleic acid molecules from other nucleic acid molecules by adjusting steps in the isolation procedure (see, below, Examples 6 and 7). Basic protocols for binding nucleic acids to magnetic particles have been described (see, e.g., PCT publication No. WO 95/01359, incorporated herein by reference). For example, nucleic acids may be isolated with the porous, magnetic, glass particles of the invention in the presence of salts in high concentrations that promote binding of the nucleic acid to the particles. Preferably, one or more chaotropic agents (as described above) is also present, such as sodium perchlorate, guanidinium hydrochloride, guanidinium isothiocyanate, potassium iodide, potassium thiocyanate, sodium chloride, sodium isothiocyanate magnesium chloride or sodium iodide. More preferably, the chaotropic agent is guanidinium isothiocyanate. A chaotropic agent is used at a concentration that is, preferably, in the range of 1 to 8 M; more preferably, in the range of 2 to 5 M; and, most preferably, in the range of 2 to 4 M. Furthermore, a $C_1$-$C_5$ aliphatic alcohol, such as methanol, ethanol, n-propanol, isopropanol, n-butanol, tert-butanol, n-pentanol, or combinations thereof, in a concentration of 1 to 80% (vol/vol) may also be added to the solution of chaotropic agent. Especially preferred is the use of isopropanol.

The concentrations of salts and/or alcohols may be adjusted so that nucleic acid molecules are bound selectively to the magnetic particles. Furthermore, it is possible to separate nucleic acids of different lengths from each other by adjusting the concentrations of chaotropic salts and/or alcohols. Examples of various buffer conditions for binding and eluting nucleic acid molecules of interest to porous, magnetic, glass particles of the invention are described below (see, Examples).

The magnetic particles to which particular nucleic acid molecules of interest are bound or adsorbed can be retrieved or separated from a mixture magnetically. For example, the particles can be attracted to the wall of the vessel containing them by applying an external magnetic field, and the contents not bound to the particles can then be removed, e.g., by pipetting, decanting, or suction filtration. In an alternative procedure, the magnetic particles with the bound nucleic acid molecules may be separated from the unbound components of a mixture by immersing a magnet into the mixture to collect the particles containing the bound nucleic acid molecules, transferring the particles on the magnet to another vessel, and, if desired, wiping or washing off the particles from the magnet into the vessel and removing the magnet stripped of the collected particles.

After the binding step, the particles may also be separated from impurities, if necessary, by washing steps with solvents and subsequent magnetic separations. The wash solution may contain alcohols, other highly volatile organic solvents such as acetone, and even one or more chaotropic agents.

If it is appropriate for further utilization of the separated nucleic acid molecules, the nucleic acid molecules may be eluted with an elution buffer from the magnetic particles. The elution buffer may contain, e.g., deionized water, aqueous solutions of low salt concentrations, Tris-[hydroxymethyl] amino methane (Tris) buffer, and/or ethylenediaminetetraacetate (EDTA).

A more complete appreciation of the invention, alternate and obvious embodiments, and the advantages thereof can also be obtained from the following non-limiting examples.

EXAMPLES

Example 1

Synthesis I: Synthesis of Porous, Magnetic, Glass Particles Using Alkaline Hydrolysis of Tetraethoxysilane Iron (II, III) oxide particles (Aldrich, Steinheim, Germany, catalog No. 31,006-9) were placed in a ball mill, such as a PM 400 planetary ball mill (Retsch, Haan, Germany), and suspended in 50 ml of isopropanol or ethanol. The mill jar was loaded with 3 mm diameter yttrium oxide balls, and the mill was run for 3 hours at maximum intensity. The milled particles were removed, the yttrium oxide particles separated according to manufacturer's procedure, and 4 g of milled iron oxide particles were transferred to a 500 ml Erlenmeyer flask fitted with a reflux condenser and a stirrer (Merck GmbH; Koeln, Germany; catalog No. 9.197215). 150 ml of absolute ethanol and 45 ml of 5 M ammonia/ammonium chloride buffer (pH 11) were added to the milled particles in the flask and mixed by stirring at 500 rpm. 100 ml of a tetraethoxysilane solution (30 ml tetraethoxysilane: 70 ml ethanol) were added dropwise with a peristaltic pump over a period of three hours at room temperature, and the reaction mixture allowed to incubate (age) for another 24 hours with continual stirring. The mixture was then suction-filtered through a porosity 3 glass frit to collect the resulting particles. The collected particles were washed twice with 100 ml deionized water, twice with 100 ml absolute ethanol, and twice more with deionized water. The particles were then dried at 120° C. in a circulating air drying oven.

Example 2

Synthesis II: Synthesis of Porous, Magnetic, Glass Particles Using Acid Hydrolysis of Tetraethoxysilane Ten grams of Magnetic Pigment 345 (BASF, Ludwigshafen, Germany) were placed in a plastic vessel and mixed with 100 ml absolute ethanol. A homogenizer stirrer (Welabo, Duesseldorf, Germany; catalog No. 333611312) was introduced into the plastic vessel, and the mixture was stirred at about 1000 rpm for 3 hours, while the plastic vessel was kept cool with an ice bath. The mixed suspension and a 100 ml ethanol rinse of the plastic vessel were transferred to a 2 liter three-neck flask, and an additional 200 ml of ethanol were added. 100 ml of a 2 M acetic acid/acetate buffer (pH 4.0) were then added to the flask. The mixture was stirred at 1000 rpm while 100 ml of a tetraethoxysilane solution (50 ml tetraethoxysilane:50 ml ethanol) were added dropwise with a dropping funnel over a period of 10 minutes. The mixture was allowed to age overnight (approximately 8-12 hours) with continual stirring, and then filtered by suction through a porosity 3 glass frit to collect the resulting particles. The resulting particles were washed twice with 100 ml of deionized water, twice with 100 ml absolute ethanol, and twice again with 100 ml of deionized water. The particles were dried for 8 hours at 120° C. in a circulating air dry oven. The resulting particles had a mean diameter of 10 µm.

Example 3

Synthesis III: Synthesis of Porous, Magnetic, Glass Particles from Magnetite and Sodium Silicate Ten grams of Magnetic Pigment 345 (BASF, Ludwigshafen, Germany) were suspended in 100 ml paraffin oil in a plastic vessel and stirred with a homogenizing stirrer at 1000 rpm for 3 hours while the plastic vessel is kept cool with an ice bath. Then, 100 ml of paraffin oil were added to the plastic vessel, and the mixture was stirred again until homogenous. The mixture was transferred to a 2 liter three-necked. An additional 200 ml of paraffin oil were added, then 200 ml of 1-hexanol (Fluka, catalog No. 52840), and 60 ml of an aqueous sodium silicate solution (27% $SiO_2$ in water, Fluka, catalog No. 71957). The mixture was then stirred at 2000 rpm, while 60 ml of concentrated acetic acid was added dropwise over a period of 5 minutes. The mixture was then stirred for an additional 60 minutes. Then the mixture containing the newly formed particles was poured into centrifugation tubes, and the tubes centrifuged for 1 hour at 4000 rpm to collect the particles. The supernatant liquid is decanted, and the particles are suspended in a methanol solution (50%). The suspension of particles was suction filtered through a porosity 3 glass frit. The collected particles are than washed twice with 100 ml of absolute ethanol, and then twice with 100 ml of deionized water. The particles were then dried in a circulating air drying oven at 200° C. The resulting porous, magnetic, glass particles had a mean diameter of 25 µm.

Example 4

Synthesis IV: Synthesis of Porous, Ferrimagnetic, Silica Particles

In a 500 ml plastic vessel, 200 ml anhydrous glycerol was added, and the vessel adjusted under a stirrer. 24 g magnetite (Bayoxide 8713 H, manufactured by Bayer AG, Leverkusen, Germany) was added slowly to the glycerol with slow stirring, and stirring was continued for two hours at 2,000 rpm to destroy agglomerations. Then, the stirring speed was reduced and 250 ml glycerol was added to the suspension. After five minutes, the reaction mixture was transferred to a 4 liter flask with stirrer (see, Example 1) and dropping funnel. 450 ml glycerol, 900 ml ethanol, and 120 ml tetraethoxysilane were added, and the stirring speed adjusted to 2,000 rpm. Within ten minutes, 300 ml of a 7 M ammonium chloride buffer, pH 10.5, were added, and the stirring speed was maintained for twelve hours. Then, the reaction mixture was filtered, washed two times with demineralized water and two times with ethanol and dried for seven hours at 300° C. The particles had a particle size of 5 to 10 µm.

Example 5

Synthesis V: Synthesis of Porous, Magnetic, Glass Particles from Magnetite and Silica Nanoparticles Ten grams of Magnetic Pigment 345 (BASF, Ludwigshafen, Germany) and 100 ml of absolute ethanol were placed in a plastic vessel and stirred with a homogenizing stirrer for 2 hours at 1000 rpm. An additional 100 ml of ethanol were added, and the mixture stirred for 5 minutes more. The contents of the vessel were transferred to a 1 liter three-necked flask. 30 ml of LUDOX AS40 (Aldrich, Deisenhofen, Germany, catalog No. 42,084-0) and 400 ml of deionized water were also added to the flask. The mixture in the flask was stirred at 1000 rpm for 5 minutes. Then 50 ml of concentrated acetic acid were added dropwise over a period of 5 minutes with continual stirring. The mixture was stirred for an additional 30 minutes at 1000 rpm and then at 500 rpm for a further 60 minutes. The mixture containing newly formed particles was suction filtered through a porosity 3 glass frit to collect the particles. The collected particles were washed twice with 100 ml of deionized water, twice with 100 ml of absolute ethanol, and twice more with 100 ml of deionized water. The suction was continued until the washed particles were dry. The particles were further dried for 7 hours at 200° C. in a circulating air drying oven. The porous, magnetic, glass particles produced by this procedure had an average diameter of 25 µm.

Example 6

Use of Porous, Magnetic, Glass Particles to Purify Plasmid DNA from Smaller Nucleic Acid Molecules This example compares the ability of three different magnetic particles to purify a plasmid DNA molecule from a mixture of shorter DNA molecules. In this example, magnetic particles from three different sources are used to separate a 3 kb plasmid vector from a mixture of polymerase chain reaction (PCR) oligonucleotide primers. The magnetic particles were obtained by the procedure in Example 4 as an example of the porous, magnetic, glass particles of the invention, from Roche Diagnostics (mRNA Isolation Kit, catalog No. 1934333, Roche Diagnostics, Mannheim, Germany), and from Promega (WIZARD PURE FECTION® Plasmid DNA Purification Systems, catalog No. A2150, Promega Corp., Madison, Wis.).

A solution of nucleic acid molecules was prepared containing the phagemid pBLUESCRIPT II, which is 2.96 kb (Stratagene GmbH, Heidelberg, Germany) and a set of commercially available oligomeric PCR primers (TIB Molbiol, Berlin, Germany), which have nucleotide lengths of 20 nucleotides (20 mer), 45 nucleotides (45 mer), 56 nucleotides (56 mer), and 75 nucleotides (75 mer), at a concentration of 1 µg of oligomer per 50 µl.

Three preparations of magnetic particles obtained from Example 4, were freed of buffer contaminants by magnetic separation, washed two times with water and two times with absolute ethanol, and vacuum dried. The particles were then suspended in buffer PB, a solution containing chaotropic agents, (QIAGEN Inc., Valencia, Calif., USA, catalog No. 19066) at a concentration of 23.5 mg/ml. 100 µl of each suspension of particles were mixed with a 50 µl aliquot of the nucleic acid molecules solution in a 500 µl PCR Eppendorf tube. The particles and nucleic acid molecules were then mixed for 1 minute on an IKA Minishaker (IKA, Staufen, Germany). The PCR tubes were then placed in a Dynal MPC-P-12 magnetic separator to collect and separate the magnetic particles from the liquid, and the supernatant liquid was then discarded. The particles were then washed by resuspending four times in buffer PE (QIAGEN Inc., Valencia, Calif., USA, catalog No. 19065).

The washed particles were dried for 15 minutes in a heating block at 37° C. to remove residual ethanol. To elute nucleic acid molecules from the particles, 30 µl of elution buffer (10 mM Tris HCl (Tris [hydroxymethyl] amino methane), pH 8.5) were added to the particles in the PCR tubes, and the tubes were then mixed for 1 minute on an IKA Minishaker. The PCR tubes were then placed in the magnetic separator, and the particles separated magnetically. 25 µl of eluate were then pipetted from the tubes. To analyze the yield of nucleic acid molecules, 15 µl samples of the eluates were run on a standard 2% TAE (Tris, acetate, EDTA (ethylene diamine tetraacetate) agarose gel containing ethidium bromide. Table 1 below shows the yields of the various nucleic acid molecules purified by the three types of magnetic particles.

TABLE 1

| Source of particle | Yield of plasmid (percent) | Yield of 20 mer (percent) | Yield of 45 mer (percent) | Yield of 56 mer (percent) | Yield of 75 mer (percent) |
|---|---|---|---|---|---|
| Example 4 | 88 | 0 | 4 | 5 | 6 |
| Boehringer | 53 | 11 | 37 | 47 | 32 |
| Promega | 80 | 0 | 23 | 33 | 38 |

The yields of nucleic acid molecules in Table 1 clearly show that the porous, magnetic, glass particles produced by the procedure in Example 4 were more effective in purifying plasmid DNA from the smaller nucleic acid molecules than either of the commercially available preparations of magnetic particles.

Example 7

Use of Porous, Magnetic, Glass Particles to Purify Genomic DNA from Whole Blood

This example demonstrates the use of porous, magnetic, glass particles of this invention to purify genomic DNA from human blood cells.

Porous, magnetic, glass particles were synthesized according to the procedure in Example 4. A protease solution was prepared by dissolving 110 mg of QIAGEN protease (QIAGEN Inc., Valencia, Calif., USA, catalog No. 19157) in nuclease free water containing 0.04% sodium azide. This protease solution is stable for at least 2 months when stored at 2-8° C. AW1 buffer was prepared by mixing 125 ml of absolute ethanol (Fluka AG. Buchs, Switzerland) with 95 ml of AW1 concentrated buffer stock (QIAGEN Inc., Valencia, Calif., USA, catalog No. 19081). AW2 buffer was prepared by mixing 160 ml of absolute ethanol with 66 ml of AW2 concentrated buffer stock (QIAGEN Inc., Valencia, Calif., USA, catalog No. 19072). Porous, magnetic, glass particles (180 mg) were suspended in 1 ml of a chaotropic AL buffer (QIAGEN Inc., Valencia, Calif., USA, catalog No. 19075), and the suspension mixed with a homogenizer (IKA Minishaker) immediately before use.

The porous, magnetic, glass particles of the invention were employed to isolate genomic DNA from blood cells using the following blood spin protocol.

20 µl of the protease solution was transferred into the bottom of a microcentrifuge tube and mixed with 200 µl of Buffer AL and with 200 µl of whole human blood in a microcentrifuge by pulse-vortexing for 15 seconds to obtain a homogenous mixture (cell extract). 20 µl of a homogenous suspension of magnetic particles in AL buffer were added, followed by pulse-vortexing the microfuge tube for 15 seconds. The mixture of magnetic particles and cell extract was then incubated at 56° C. for 10 minutes. 250 µl isopropanol were added to the mixture, and the microfuge tube was immediately pulse-vortexed for 15 seconds.

The microfuge tube containing the magnetic particles and cell extract was placed on a magnetic separator (Dynal AS, see above) to separate the magnetic particles from the supernatant liquid, which was then discarded. The particles were washed twice with 500 µl of Buffer AW1, by resuspending the particles in the buffer and vortexing briefly to thoroughly suspend the particles. After each vortexing, the particles were collected using the magnetic separator. In the same manner, the particles were then washed twice with 500 µl of Buffer AW2. After this set of washes, the final wash buffer was removed, and the tube was allowed to set in the magnetic separator for 15 minutes at room temperature to permit the particles to dry and to remove residual ethanol by volatilization.

After this drying period, the DNA bound to the magnetic particles was eluted by suspending the particles in 100 µl of Buffer AE (QIAGEN Inc., Valencia, Calif., USA, catalog No. 19077), vortexing briefly to suspend the particles, and incubating the suspension for 1 minute at room temperature. The magnetic particles were then collected and separated from the eluate using the magnetic separator. The supernatant eluate was transferred to another microfuge tube. This elution step was repeated.

The length and purity of the genomic DNA obtained by this procedure was determined by running a sample of the eluted DNA on a standard 1% TAE agarose gel containing ethidium bromide. The yield and purity were assessed by the ratio of the absorbance at 260 nm ($A_{260}$) to the absorbance at 280 nm ($A_{280}$) in a spectrophotometer. Typically, this procedure yielded 4-8 µg of purified genomic DNA per microfuge tube (200 µl whole blood) with an average ratio of $A_{260}/A_{280}$ between 1.6 and 1.85.

Other variations and embodiments of the invention described herein will now be apparent to those of ordinary skill in the art without departing from the spirit of the invention or the scope of the claims below. All patents, applications, and publications cited in the above text are incorporated herein by reference.

What is claimed is:

1. A method of isolating a molecule of interest from a mixture, comprising:
   a) providing a mixture containing a molecule of interest;
   b) contacting the mixture with porous, ferro- or ferrimagnetic, dried glass particles comprising silica glass precipitated or adsorbed on ferro- or ferrimagnetic iron oxide particles or pigments, wherein said porous, ferro- or ferrimagnetic, glass particles retain their ferro- or ferrimagnetic properties by having been maintained at a selected temperature between about 200° C. and about 500° C. for a period of hours to dry said particles, and wherein said temperature is below the Curie temperature of said particles;
   c) allowing the molecule of interest in the mixture to adhere to the porous, ferro- or ferrimagnetic, glass particles;
   d) collecting the porous, ferro- or ferrimagnetic, glass particles containing the adherent molecule of interest by applying an external magnetic field; and
   e) removing the porous, ferro- or ferrimagnetic, glass particles with the adherent molecule of interest from the unbound components of the mixture.

2. The method of isolating a molecule of interest from a mixture according to claim 1, further comprising the step of eluting the adherent molecule of interest from the porous, ferro- or ferrimagnetic, glass particles.

3. The method of isolating a molecule of interest from a mixture according to claim 1, wherein the molecule of interest is selected from the group consisting of nucleic acids, proteins, polypeptides, peptides, carbohydrates, lipids, and combinations thereof.

4. The method of isolating a molecule of interest from a mixture according to claim 3, wherein the molecule of interest is a nucleic acid molecule.

5. The method of isolating a nucleic acid according to claim 4, wherein the nucleic acid is selected from the group consisting of plasmid DNA, genomic DNA, cDNA, PCR DNA, linear DNA, RNA, ribozymes, aptamers, and chemically synthesized nucleic acids.

6. The method of isolating a molecule of interest from a mixture according to claim 2, wherein the molecule of interest is selected from the group consisting of nucleic acids, proteins, polypeptides, peptides, carbohydrates, lipids, and combinations thereof.

7. The method of isolating a molecule of interest from a mixture according to claim 6, wherein the molecule of interest is a nucleic acid molecule.

8. The method of isolating a nucleic acid according to claim 7, wherein the nucleic acid is selected from the group consisting of plasmid DNA, genomic DNA, cDNA, PCR DNA, linear DNA, RNA, ribozymes, aptamers, and chemically synthesized nucleic acids.

9. The method of claim 1, wherein the glass particles have a diameter of about 5 µm to about 25 µm.

10. The method of claim 9, wherein the glass particles have a diameter of about 7 µm to about 10 µm.

11. The method of claim 1, wherein the glass particles have a BET specific surface area of about 190 $m^2/g$ to about 270 $m^2/g$.

12. The method of claim 1, wherein said porous, ferro- or ferrimagnetic, glass particles retain their ferro- or ferrimagnetic properties when dried at a temperature of about 300° C.

13. A method of isolating a nucleic acid of interest from a mixture, comprising:
   a) providing a mixture containing a nucleic acid of interest;
   b) contacting the mixture with one or more chaotropic agents and porous, ferro- or ferrimagnetic, dried glass particles comprising silica glass precipitated or adsorbed on ferro- or ferrimagnetic iron oxide particles or pigments, wherein said porous, ferro- or ferrimagnetic, glass particles retain their ferro- or ferrimagnetic properties by having been maintained at a selected temperature between about 200° C. and about 500° C. for a period of hours to dry said particles, and wherein said temperature is below the Curie temperature of said particles;

c) allowing the nucleic acid of interest in the mixture to adhere to the porous, ferro- or ferrimagnetic, glass particles;
d) collecting the porous, ferro- or ferrimagnetic, glass particles containing the adherent nucleic acid of interest by applying an external magnetic field; and
e) removing the porous, ferro- or ferrimagnetic, glass particles with the adherent nucleic of interest from the unbound components of the mixture.

14. The method of isolating a nucleic acid of interest from a mixture according to claim 13, further comprising the step of eluting the adherent nucleic acid of interest from the porous, ferro- or ferrimagnetic, glass particles.

15. The method of isolating a nucleic acid according to claim 13, wherein the nucleic acid is selected from the group consisting of plasmid DNA, genomic DNA, cDNA, PCR DNA, linear DNA, RNA, ribozymes, aptamers, and chemically synthesized nucleic acids.

16. The method of claim 13, wherein the glass particles have a diameter of about 5 μm to about 25 μm.

17. The method of claim 16, wherein the glass particles have a diameter of about 7 μm to about 10 μm.

18. The method of claim 13, wherein the glass particles have a BET specific surface area of about 190 $m^2/g$ to about 270 $m^2/g$.

19. The method of claim 13, wherein the one or more chaotropic agents is selected from the group consisting of sodium perchlorate, guanidinium hydrochloride, guanidinium isothiocyanate, potassium iodide, potassium thiocyanate, sodium chloride, sodium isothiocyanate magnesium chloride and sodium iodide.

20. The method of claim 19, wherein the chaotropic agent is guanidinium isothiocyanate.

21. The method of claim 13, wherein b) further comprises contacting the mixture with a $C_1$-$C_5$ aliphatic alcohol, selected from the group consisting methanol, ethanol, n-propanol, isopropanol, n-butanol, tert-butanol, n-pentanol, and combinations thereof.

22. The method of claim 13, wherein said porous, ferro- or ferromagnetic, glass particles retain their ferro- or ferrimagnetic properties when dried at a temperature of about 300° C.

* * * * *